United States Patent
Ferguson (10) Patent No.: US 10,857,041 B2
(45) Date of Patent: Dec. 8, 2020

(54) REUSABLE DIAPER ASSEMBLY

(71) Applicant: Cherry Ferguson, Pompano Beach, FL (US)

(72) Inventor: Cherry Ferguson, Pompano Beach, FL (US)

( * ) Notice: Subject to any disclaimer, the term of this patent is extended or adjusted under 35 U.S.C. 154(b) by 417 days.

(21) Appl. No.: 15/792,138

(22) Filed: Oct. 24, 2017

(65) Prior Publication Data

US 2019/0117470 A1   Apr. 25, 2019

(51) Int. Cl.
*A61F 13/505* (2006.01)
*A61F 13/15* (2006.01)
*A61F 13/49* (2006.01)

(52) U.S. Cl.
CPC ...... *A61F 13/505* (2013.01); *A61F 13/15268* (2013.01); *A61F 13/49004* (2013.01)

(58) Field of Classification Search
CPC .......... A61F 13/49003; A61F 13/49004; A61F 13/01; A61F 13/5268; A61F 13/505; A61F 13/513; A61F 13/15699; A61F 2013/15276; A61F 2013/5055

See application file for complete search history.

(56) References Cited

U.S. PATENT DOCUMENTS

| | | | |
|---|---|---|---|
| 4,770,656 A * | 9/1988 | Proxmire | A61F 13/49007 604/393 |
| 4,955,880 A | 9/1990 | Rodriquez | |
| 5,207,662 A | 5/1993 | James | |
| 5,417,680 A * | 5/1995 | Kimura | A61F 13/49473 604/385.28 |
| 6,092,242 A * | 7/2000 | Niedermeyer | A41B 9/008 2/400 |
| 6,419,666 B1 * | 7/2002 | Mishima | A61F 13/49473 604/385.01 |
| 6,443,933 B1 * | 9/2002 | Suzuki | A61F 13/4942 604/358 |
| 6,551,296 B1 * | 4/2003 | Boulanger | A61F 13/4752 604/385.04 |
| D621,501 S | 8/2010 | Coon | |
| 9,060,905 B2 | 6/2015 | Wang et al. | |
| 9,301,551 B2 | 4/2016 | Back et al. | |

(Continued)

FOREIGN PATENT DOCUMENTS

| | | | | |
|---|---|---|---|---|
| CA | 2265430 A1 * | 9/1999 | | A61F 13/474 |
| GB | 2256803 A * | 12/1992 | | A61F 13/505 |

(Continued)

*Primary Examiner* — Susan S Su (57) ABSTRACT

A reusable diaper assembly includes a diaper that may be worn on a child. A first mating member is coupled to the diaper and a second mating member is coupled to the diaper. A first fastener is coupled to the diaper and the first mating member is matable to the first fastener to retain the diaper on the child. A second fastener is coupled to the diaper and the second mating member is matable to the second fastener to retain the diaper on the child. An absorbing unit is removably coupled to the diaper. The absorbing unit is comprised of a fluid absorbent material to absorb waste from the child. Moreover, the absorbing unit is selectively removed from the diaper to be disposed of when the absorbing unit becomes soaked with the waste. In this way the diaper may be re-used.

8 Claims, 6 Drawing Sheets

(56) References Cited

U.S. PATENT DOCUMENTS

| | | | | |
|---|---|---|---|---|
| 2001/0027304 | A1* | 10/2001 | Mayer | A61F 13/505 604/385.14 |
| 2002/0143316 | A1* | 10/2002 | Sherrod | A61F 13/505 604/385.101 |
| 2003/0135185 | A1* | 7/2003 | Crowther | A61F 13/15739 604/385.01 |
| 2003/0216705 | A1* | 11/2003 | Coates | A61F 13/495 604/386 |
| 2014/0013490 | A1* | 1/2014 | Evenson | A61F 13/496 2/400 |
| 2014/0188067 | A1* | 7/2014 | Herron | A61F 13/49 604/385.01 |
| 2014/0303589 | A1* | 10/2014 | Paz | A61F 13/505 604/395 |
| 2015/0216739 | A1 | 8/2015 | Datwyler et al. | |
| 2016/0278999 | A1 | 9/2016 | Wang et al. | |
| 2018/0228665 | A1* | 8/2018 | Relekar | A61F 13/5611 |

FOREIGN PATENT DOCUMENTS

| | | | | |
|---|---|---|---|---|
| GB | 2540151 A | * | 1/2017 | A41B 9/00 |
| WO | WO2016138466 | | 9/2016 | |

* cited by examiner

REUSABLE DIAPER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to diaper devices and more particularly pertains to a new diaper device having a removable, absorbent pad and a diaper.

BRIEF SUMMARY OF THE INVENTION

An embodiment of the disclosure meets the needs presented above by generally comprising a diaper that may be worn on a child. A first mating member is coupled to the diaper and a second mating member is coupled to the diaper. A first fastener is coupled to the diaper and the first mating member is matable to the first fastener to retain the diaper on the child. A second fastener is coupled to the diaper and the second mating member is matable to the second fastener to retain the diaper on the child. An absorbing unit is removably coupled to the diaper. The absorbing unit is comprised of a fluid absorbent material to absorb waste from the child. Moreover, the absorbing unit is selectively removed from the diaper to be disposed of when the absorbing unit becomes soaked with the waste. In this way the diaper may be re-used.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 6 thereof, a new diaper device embodying the principles and concepts of an embodiment of the disclosure and generally designated by the reference numeral 10 will be described.

As best illustrated in FIGS. 1 through 6, the reusable diaper assembly 10 generally comprises a diaper 12 that may be worn on a child. The diaper 12 has a first surface 14, a second surface 16 and a perimeter edge 18 extending therebetween. The perimeter edge 18 has a front side 20, a back side 22, a first lateral side 26 and a second lateral side 24. Moreover, the diaper 12 is elongated between the front 20 and back 22 sides. The first surface 14 is positioned on the child's crotch having the front side 20 positioned on the child's stomach and having the back side 22 positioned on the child's back. The diaper 12 is comprised of an organic material such as cotton or the like. Moreover, the diaper 12 is re-usable and the diaper 12 may be selectively laundered.

A first elastic member 28 is positioned between the first 14 and second 16 surfaces. The first elastic member 28 is partially coextensive with the first lateral side 26 to bias the first lateral side 26 around the child's crotch. A second elastic member 30 is positioned between the first 14 and second 16 surfaces. The second elastic member 30 is partially coextensive with the second lateral side 24 to bias the second lateral side 24 around the child's crotch.

A first mating member 34 is coupled to the diaper 12. The first mating member 34 is positioned on the first lateral side 26 and is aligned with the back side 22. The first mating member 34 is partially comprised of an elastic material such as elastic or the like. A second mating member 32 is coupled to the diaper 12. The second mating member 32 is positioned on the second lateral side 24 and is aligned with the back side 22. The second mating member 32 is partially comprised of an elastic material such as elastic or the like.

A first fastener 36 is coupled to the second surface 16 of the diaper 12. The first fastener 36 is aligned with an intersection between the first lateral side 26 and the front side 20. The first mating member 34 is matable to the first fastener 36 to retain the diaper 12 on the child. Each of the first fastener 36 and the first mating member 32 may comprise complementary hook and loop fasteners or the like.

A second fastener 38 is coupled to the second surface 16 of the diaper 12. The second fastener 38 is aligned with an intersection between the second lateral side 24 and the front side 20. The second mating member 32 is matable to the second fastener 38 to retain the diaper 12 on the child. Each of the second fastener 38 and the second mating member 34 may comprise complementary hook and loop fasteners or the like.

An absorbing unit 40 is provided and the absorbing unit 40 is removably coupled to the diaper 12. The absorbing unit 40 is aligned with the child's genitalia when the diaper 12 is worn on the child. The absorbing unit 40 is comprised of a fluid absorbent material to absorb waste from the child. Moreover, the absorbing unit 40 is selectively removed from the diaper 12. In this way the absorbing unit 40 is disposed of when the absorbing unit 40 becomes soaked with the waste thereby facilitating the diaper 12 to be re-used.

The absorbing unit 40 comprises a panel 42 that has a first side 44 and a second side 46 and the panel 42 is comprised of a fluid impermeable material. The first side 44 abuts the first surface 14 of the diaper 12 to inhibit the waste from contacting the diaper 12. Additionally, the panel 42 is positioned between the first 28 and second 30 elastic members. An adhesive layer 48 is positioned on the first side of the panel 42. The adhesive layer 48 adhesively engages the first surface 14 of the diaper 12 such that the panel 42 is removably retained on the diaper 12.

A first pad 50 is provided that has a first side 52, a second side 54 and a peripheral edge 56. The first side 52 of the first pad 50 is coupled to the second side 46 of the panel 42 and the first pad 50 substantially covers the panel 42. The first pad 50 is comprised of a fluid absorbent material to absorb the waste. Moreover, the panel 42 is wrapped upwardly along the peripheral edge 56 to inhibit the waste from leaving the first pad 50.

A second pad 58 is provided that has a first side 60, a second side 62 and a peripheral edge 64. The first side 60 of the second pad 58 is coupled to the second side 54 of the first pad 50. Thus, the second side 62 of the second pad 58 abuts the child's crotch when the diaper 12 is worn. The second pad 58 completely covers the first pad 50.

The second pad 58 is comprised of a fluid absorbent material to absorb the waste. Moreover, the second pad 58 is comprised of a fluid wicking material to wick the waste into the first pad 50. In this way the second pad 58 inhibits the waste from contacting the child's skin. The panel 42 is wrapped upwardly along the peripheral edge 64 of the second pad 58 to inhibit the waste from leaving the second pad 58.

Figure 1:
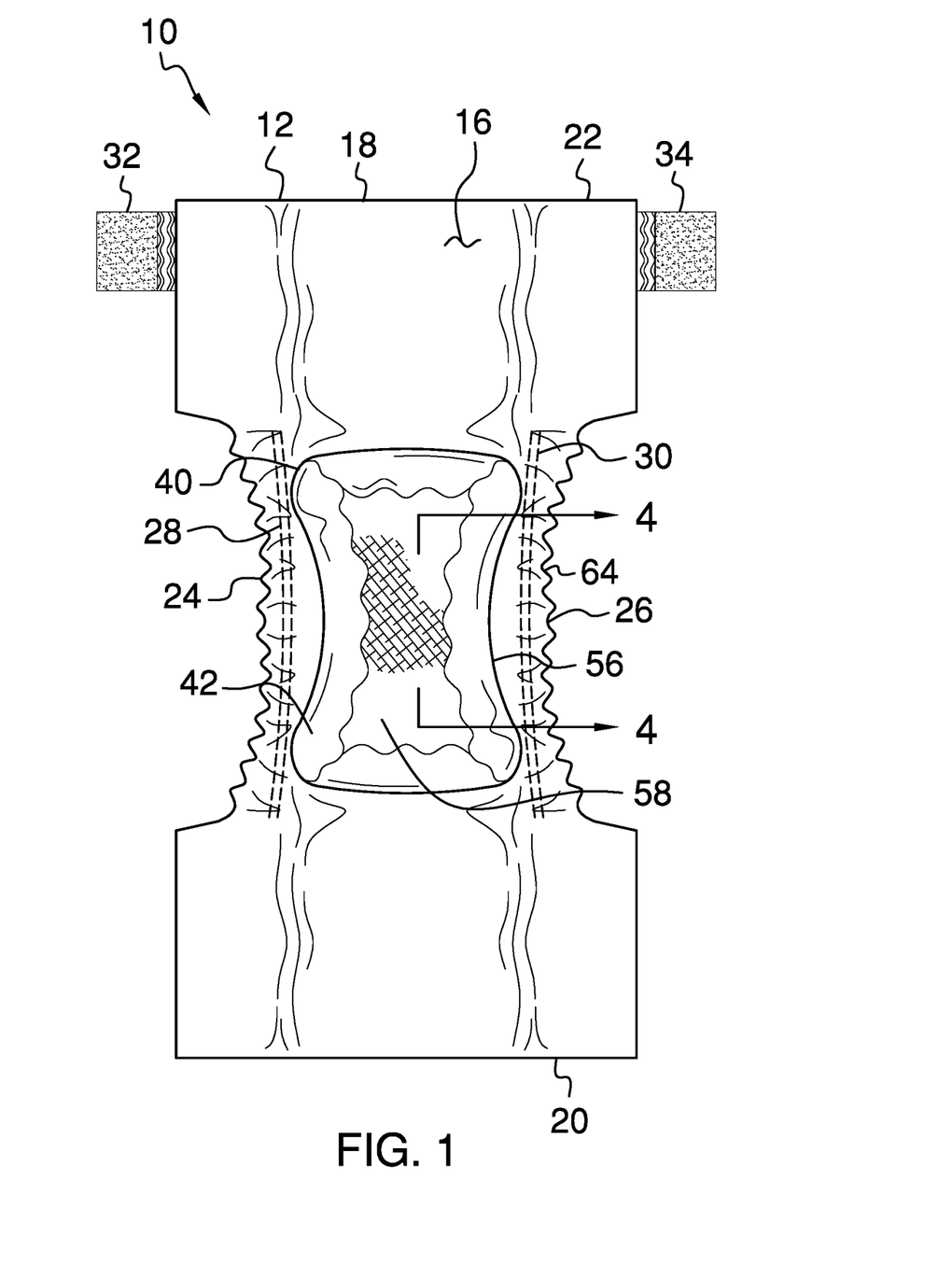
FIG. 1 is a top view of a reusable diaper assembly according to an embodiment of the disclosure.
Figure 2:
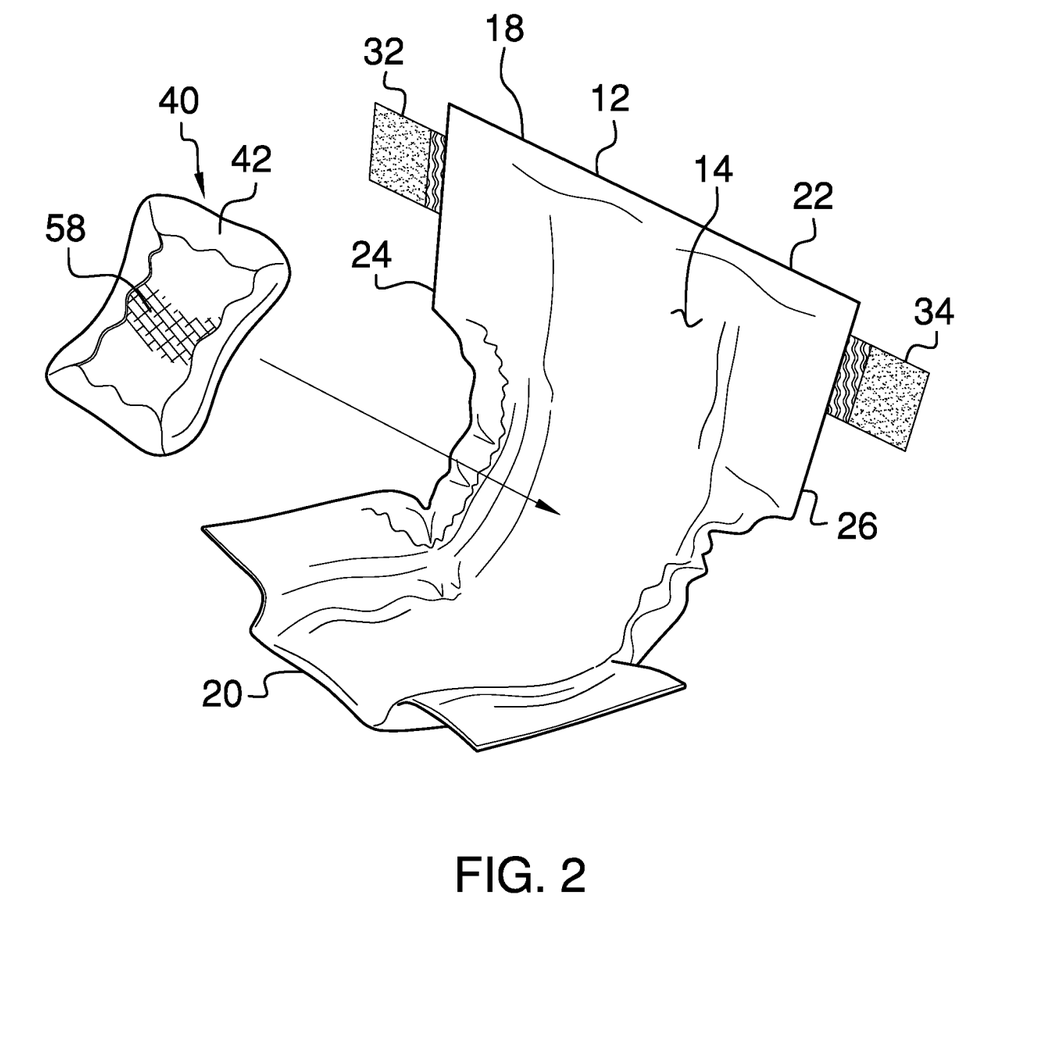
FIG. 2 is an exploded perspective view of an embodiment of the disclosure.
Figure 3:
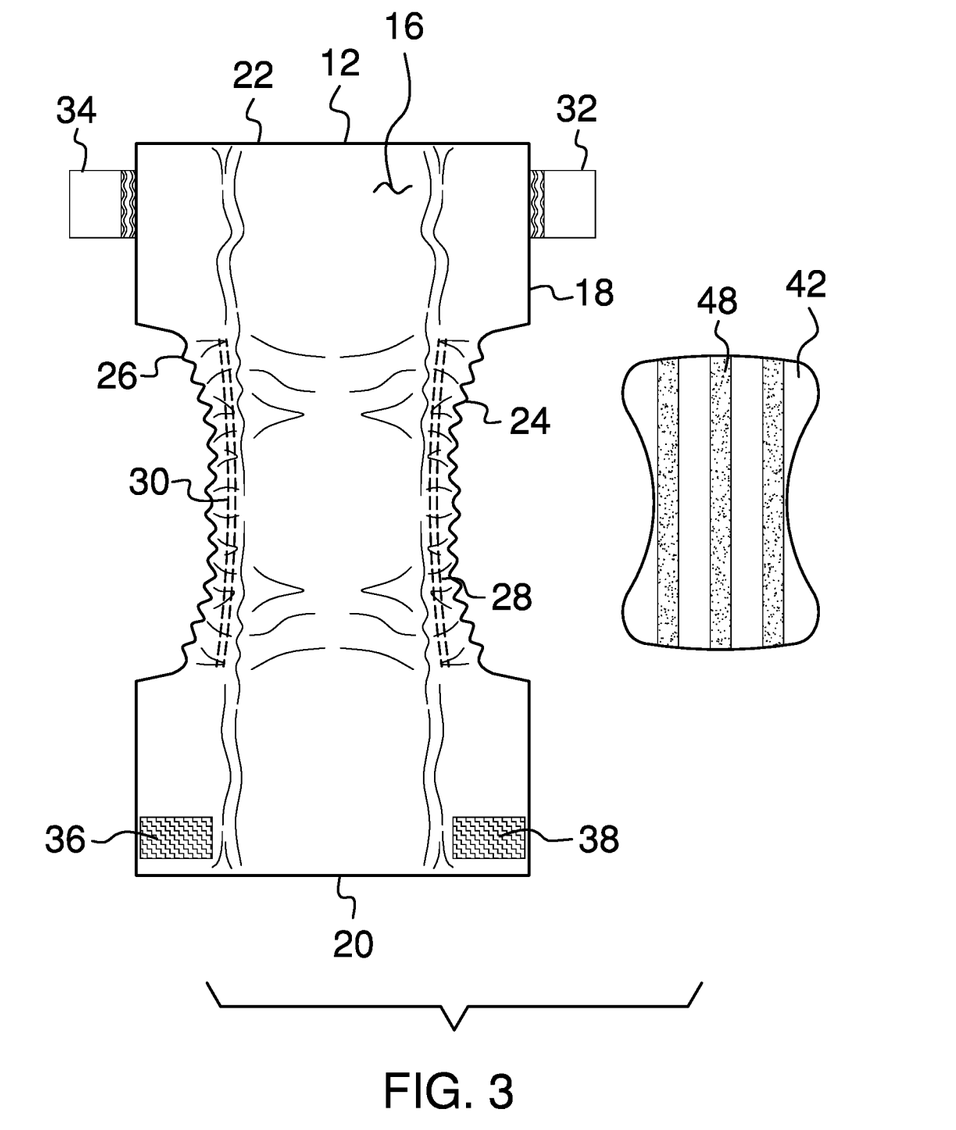
FIG. 3 is a bottom perspective view of an embodiment of the disclosure.
Figure 4:
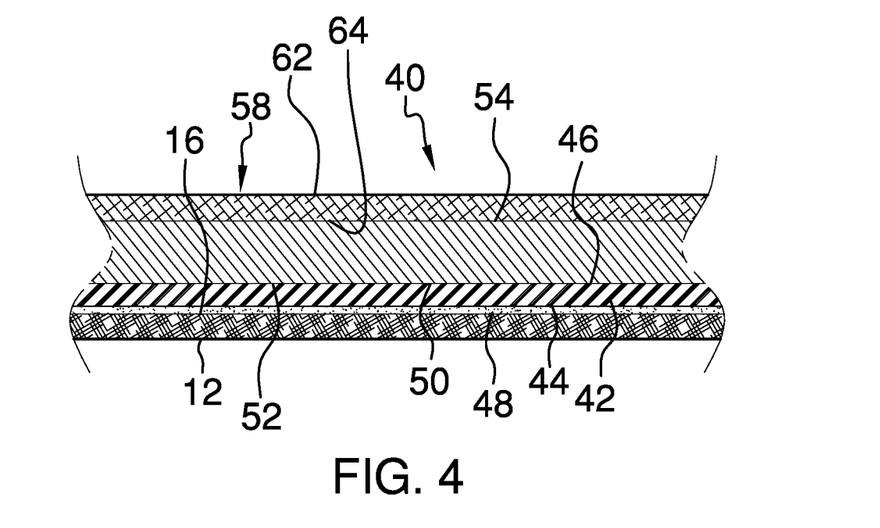
FIG. 4 is a cross sectional view taken along line 4-4 of FIG. 1 of an embodiment of the disclosure.
Figure 5:
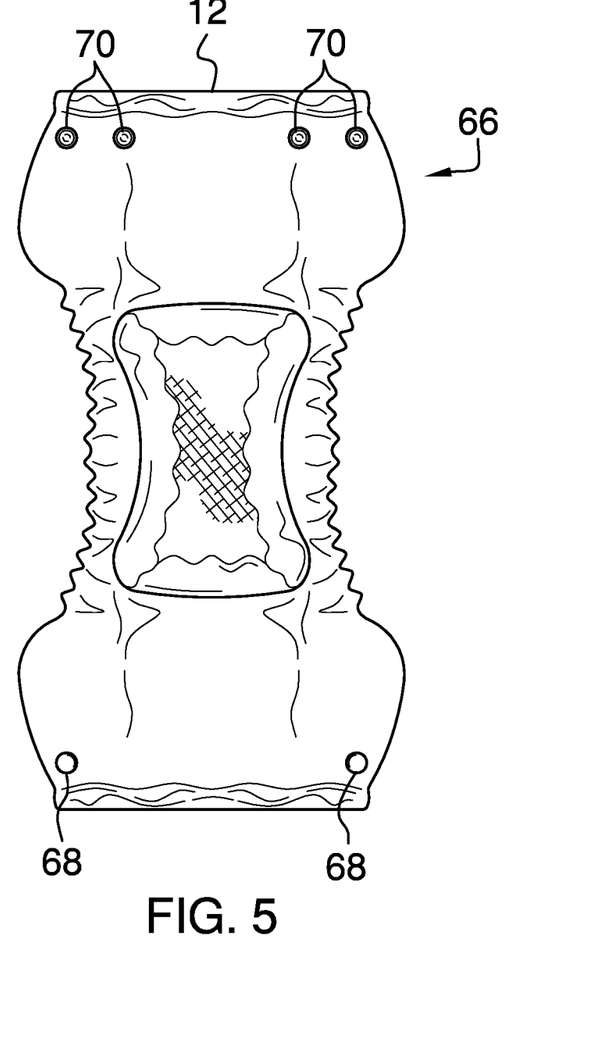
FIG. 5 is a perspective view of an alternative embodiment of the disclosure.

In an alternative embodiment 66 as shown in FIG. 5, a pair of first snaps 68 may be coupled to the diaper 12. Each of the first snaps 68 may be spaced apart from each other and be aligned with the front side 20 of the diaper 12. A plurality of second snaps 70 may be coupled to the diaper 12. Each of the second snaps 70 may be spaced apart from each other and be aligned with the back side 22 of the diaper 12. Selected ones of the second snaps 70 may be manipulated to engage an associated one of the first snaps 68. In this way the diaper 12 may be retained on the child.

Figure 6:
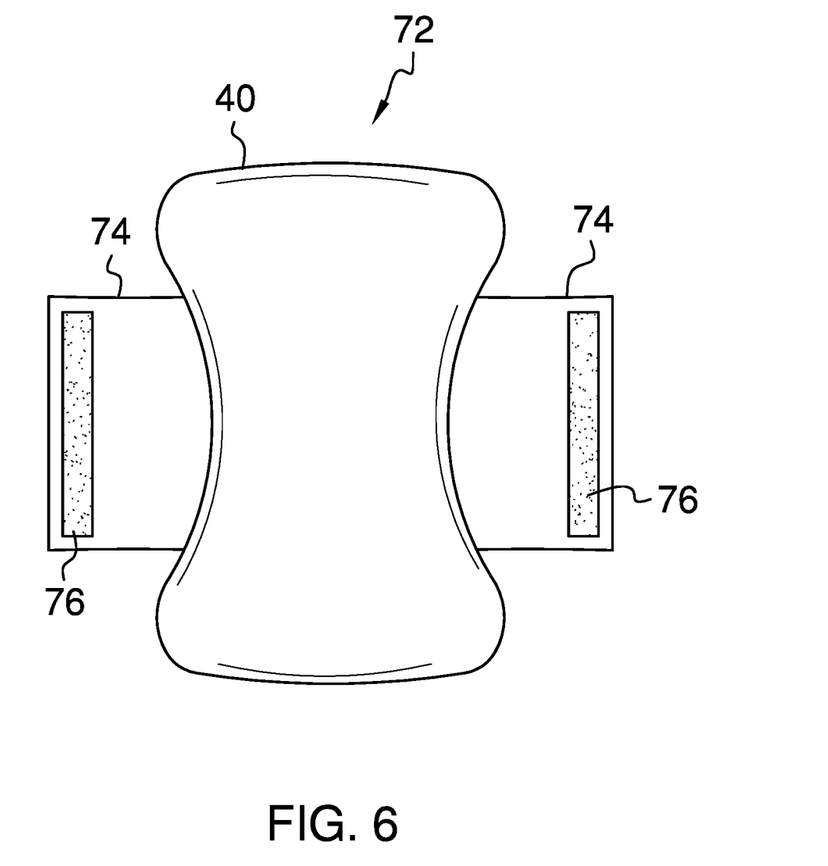
FIG. 6 is a front view of an alternative embodiment of the disclosure.

In an alternative embodiment 72 as shown in FIG. 6, a pair of flaps 74 may each extend laterally away from the absorbing unit 40. Moreover, each of the flaps 74 may be positioned on opposite lateral sides of the absorbing unit 40. Each of the flaps 74 may extend beyond a corresponding one of the first lateral side 26 and second lateral side 24 of the diaper 12 when absorbing unit 40 is positioned on the diaper 12. An adhesive strip 76 may be positioned on each of the flaps 74 to engage the diaper 12 thereby retaining each of the flaps 74 to be wrapped around the corresponding first 26 and second 24 lateral sides. Thus, the flaps 74 inhibit the diaper 12 from becoming soiled.

In use, the absorbing unit 40 is positioned on the diaper 12 having the adhesive layer 48 engage the diaper 12. The diaper 12 is placed on the child and each of the first 34 and second 32 mating members is fastened to the corresponding first 36 and second 38 fasteners. The elastic qualities of the first 34 and second 32 mating members facilitate the diaper 12 to accommodate a variety of sizes of children. The diaper 12 is removed from the child and the absorbing unit 40 is removed from the diaper 12 when the absorbing unit 40 has become soaked with the waste. Additionally, the absorbing unit 40 is discarded and a new absorbing unit 40 is positioned on the diaper 12. In this way the diaper 12 is re-used thereby reducing waste associated with changing diapers.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A reusable diaper assembly having a disposable absorbent pad being configured to be worn on a child, said assembly comprising:
   a diaper being configured to be worn on the child, said diaper having a first surface, a second surface and a perimeter edge extending therebetween, said perimeter edge having a front side, a back side, a first lateral side and a second lateral side, said diaper being elongated between said front and back sides, said first surface being configured to be positioned on the child's crotch having said front side being positioned on the child's stomach and having said back side being positioned on the child's back;
   a first elastic member being positioned between said first and second surfaces, said first elastic member being partially coextensive with said first lateral side wherein said first elastic member is configured to bias said first lateral side around the child's crotch;

a second elastic member being positioned between said first and second surfaces, said second elastic member being partially coextensive with said second lateral side wherein said second elastic member is configured to bias said second lateral side around the child's crotch;
a first mating member being coupled to said diaper;
a second mating member being coupled to said diaper;
a first fastener being coupled to said diaper, said first mating member being matable to said first fastener to retain said diaper on the child;
a second fastener being coupled to said diaper, said second mating member being matable to said second fastener to retain said diaper on the child;
an absorbing unit being removably coupled to said diaper wherein said absorbing unit is configured to be aligned with the child's genitalia, said absorbing unit being comprised of a fluid absorbent material wherein said absorbing unit is configured to absorb waste from the child, said absorbing unit being selectively removed from said diaper wherein said absorbing unit is configured to be disposed of when said absorbing unit becomes soaked with the waste thereby facilitating said diaper to be re-used, said absorbing unit comprising a panel having a first side and a second side, said panel being comprised of a fluid impermeable material, said first side abutting said second surface of said diaper wherein said panel is configured to inhibit the waste from contacting said diaper, said panel being positioned between said first and second elastic members; and
a pair of flaps extending laterally away from the absorbing unit, each flap extends beyond and wraps around a corresponding one of the first lateral side and the second lateral side to engage the diaper when the absorbing unit is positioned on the diaper.

2. The assembly according to claim 1, wherein:
said first mating member is positioned on said first lateral side and being aligned with said back side, said first mating member being comprised of an elastic material wherein said first mating member is configured to be stretched; and
said first fastener is positioned on said second surface of said diaper, said first fastener being aligned with an intersection between said first lateral side and said front side.

3. The assembly according to claim 1, wherein:
said second mating member is positioned on said second lateral side and being aligned with said back side, said second mating member being comprised of an elastic material wherein said second mating member is configured to be stretched; and
said second fastener is positioned on said second surface of said diaper, said second fastener being aligned with an intersection between said second lateral side and said front side, said second mating member being matable to said second fastener to retain said diaper on the child.

4. The assembly according to claim 1, further comprising an adhesive layer being positioned on said first side of said panel, said adhesive layer adhesively engaging said first surface of said diaper such that said panel is removably retained on said diaper.

5. The assembly according to claim 1, further comprising a first pad having a first side, a second side and a peripheral edge, said first side of said first pad being coupled to said second side of said panel, said first pad substantially covering said panel, said first pad being comprised of a fluid absorbent material wherein said first pad is configured to absorb the waste, said panel being wrapped upwardly along said peripheral edge wherein said panel is configured to inhibit the waste from leaving said first pad.

6. The assembly according to claim 5, further comprising a second pad having a first side, a second side and a peripheral edge, said first side of said second pad being coupled to said second side of said first pad wherein said second side of said second pad is configured to abut the child's crotch, said second pad completely covering said first pad, said second pad being comprised of a fluid absorbent material wherein said second pad is configured to absorb the waste.

7. The assembly according to claim 6, wherein said second pad is comprised of a fluid wicking material wherein said second pad is configured to wick the waste into said first pad thereby inhibiting the waste from contacting the child's skin, said panel being wrapped upwardly along said peripheral edge of said second pad wherein said panel is configured to inhibit the waste from leaving said second pad.

8. A reusable diaper assembly having a disposable absorbent pad being configured to be worn on a child, said assembly comprising:
a diaper being configured to be worn on the child, said diaper having a first surface, a second surface and a perimeter edge extending therebetween, said perimeter edge having a front side, a back side, a first lateral side and a second lateral side, said diaper being elongated between said front and back sides, said first surface being configured to be positioned on the child's crotch having said front side being positioned on the child's stomach and having said back side being positioned on the child's back;
a first elastic member being positioned between said first and second surfaces, said first elastic member being partially coextensive with said first lateral side wherein said first elastic member is configured to bias said first lateral side around the child's crotch;
a second elastic member being positioned between said first and second surfaces, said second elastic member being partially coextensive with said second lateral side wherein said second elastic member is configured to bias said second lateral side around the child's crotch;
a first mating member being coupled to said diaper, said first mating member being positioned on said first lateral side and being aligned with said back side, said first mating member being comprised of an elastic material wherein said first mating member is configured to be stretched;
a second mating member being coupled to said diaper, said second mating member being positioned on said second lateral side and being aligned with said back side, said second mating member being comprised of an elastic material wherein said second mating member is configured to be stretched;
a first fastener being coupled to said diaper, said first fastener being positioned on said second surface of said diaper, said first fastener being aligned with an intersection between said first lateral side and said front side, said first mating member being matable to said first fastener to retain said diaper on the child;
a second fastener being coupled to said diaper, said second fastener being positioned on said second surface of said diaper, said second fastener being aligned with an intersection between said second lateral side and said front side, said second mating member being matable to said second fastener to retain said diaper on the child;

an absorbing unit being removably coupled to said diaper wherein said absorbing unit is configured to be aligned with the child's genitalia, said absorbing unit being comprised of a fluid absorbent material wherein said absorbing unit is configured to absorb waste from the child, said absorbing unit being selectively removed from said diaper wherein said absorbing unit is configured to be disposed of when said absorbing unit becomes soaked with the waste thereby facilitating said diaper to be re-used, said absorbing unit comprising:

a panel having a first side and a second side, said panel being comprised of a fluid impermeable material, said first side abutting said first surface of said diaper wherein said panel is configured to inhibit the waste from contacting said diaper, said panel being positioned between said first and second elastic members, an adhesive layer being positioned on said first side of said panel, said adhesive layer adhesively engaging said first surface of said diaper such that said panel is removably retained on said diaper, a first pad having a first side, a second side and a peripheral edge, said first side of said first pad being coupled to said second side of said panel, said first pad substantially covering said panel, said first pad being comprised of a fluid absorbent material wherein said first pad is configured to absorb the waste, said panel being wrapped upwardly along said peripheral edge wherein said panel is configured to inhibit the waste from leaving said first pad, and a second pad having a first side, a second side and a peripheral edge, said first side of said second pad being coupled to said second side of said first pad wherein said second side of said second pad is configured to abut the child's crotch, said second pad completely covering said first pad, said second pad being comprised of a fluid absorbent material wherein said second pad is configured to absorb the waste, said second pad being comprised of a fluid wicking material wherein said second pad is configured to wick the waste into said first pad thereby inhibiting the waste from contacting the child's skin, said panel being wrapped upwardly along said peripheral edge of said second pad wherein said panel is configured to inhibit the waste from leaving said second pad; and a pair of flaps extending laterally away from the absorbing unit, each flap extends beyond and wraps around a corresponding one of the first lateral side and the second lateral side to engage the diaper when the absorbing unit is positioned on the diaper.

* * * * *